US011434456B2

(12) United States Patent
Sim et al.

(10) Patent No.: US 11,434,456 B2
(45) Date of Patent: Sep. 6, 2022

(54) TRANSPARENT PHOTOBIOREACTOR FOR SCALE-UP CULTURE OF PHOTOSYNTHETIC ORGANISMS AND METHOD FOR FABRICATING THE SAME

(71) Applicant: KOREA UNIVERSITY RESEARCH AND BUSINESS FOUNDATION, Seoul (KR)

(72) Inventors: Sang Jun Sim, Seoul (KR); Hoang Minh Pham, Seoul (KR); Byung-Sun Yu, Cheonan-si (KR); Jeongseop Lee, Seoul (KR); Young Joon Sung, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 813 days.

(21) Appl. No.: 16/146,380

(22) Filed: Sep. 28, 2018

(65) Prior Publication Data

US 2019/0100719 A1 Apr. 4, 2019

(30) Foreign Application Priority Data

Sep. 29, 2017 (KR) .......................... 10-2017-0126877
Aug. 14, 2018 (KR) .......................... 10-2018-0094946

(51) Int. Cl.
*C12M 1/00* (2006.01)

(52) U.S. Cl.
CPC ............ *C12M 21/02* (2013.01); *C12M 23/22* (2013.01); *C12M 27/20* (2013.01); *C12M 29/06* (2013.01)

(58) Field of Classification Search
CPC ...... C12M 21/02; C12M 23/22; C12M 27/20; C12M 29/06
See application file for complete search history.

(56) References Cited

U.S. PATENT DOCUMENTS

| 8,642,326 | B1 * | 2/2014 | Schaefer ................ C12M 21/02 |
| | | | 435/257.1 |
| 2004/0048364 | A1 * | 3/2004 | Trosch .................. C12M 27/20 |
| | | | 435/292.1 |

(Continued)

FOREIGN PATENT DOCUMENTS

| CN | 105733924 A | 7/2016 | |
| EP | 2228432 A1 * | 9/2010 | .......... B01F 3/04269 |

(Continued)

OTHER PUBLICATIONS

EP2228432 Machine Translation accessed Mar. 16, 2022 (Year: 2022).*

(Continued)

*Primary Examiner* — William H. Beisner
*Assistant Examiner* — Danielle B Henkel
(74) *Attorney, Agent, or Firm* — NSIP Law

(57) ABSTRACT

The present invention relates to a large-scale photosynthetic bioreactor in which transparent photobioreactors including a baffle are connected in parallel or in series by an adhesive element so that the reactor volume can be easily scaled up for scale-up culture of photosynthetic organisms, and to a fabrication method thereof. The large-scale photosynthetic bioreactor according to the present invention makes it possible to culture a larger amount of microalgae than a conventional photobioreactor in the same area. In addition, it has high light transmittance, produces a large amount of biomass per unit area due to smooth mixing, and has a significant effect of reducing carbon dioxide. Furthermore, the present invention has an advantage in that the number of photosynthetic bioreactors required to culture the same scale of photosynthetic organisms is significantly smaller than that in a conventional process for culture of photosynthetic organisms, and thus the operating costs can be reduced.

10 Claims, 12 Drawing Sheets
(8 of 12 Drawing Sheet(s) Filed in Color)

(56) References Cited

U.S. PATENT DOCUMENTS

| | | | | |
|---|---|---|---|---|
| 2009/0130706 A1* | 5/2009 | Berzin | ............ | C12M 21/02 |
| | | | | 435/41 |
| 2010/0028976 A1* | 2/2010 | Hu | ............ | C12M 23/02 |
| | | | | 435/257.1 |
| 2010/0203624 A1* | 8/2010 | Singh | ............ | B01F 11/0017 |
| | | | | 435/289.1 |
| 2013/0230904 A1* | 9/2013 | Suryo | ............ | C12M 31/06 |
| | | | | 435/257.1 |
| 2013/0309762 A1* | 11/2013 | Sim | ............ | C12M 21/02 |
| | | | | 435/292.1 |
| 2014/0263090 A1* | 9/2014 | Yencho | ............ | C02F 1/325 |
| | | | | 210/748.11 |
| 2018/0237734 A1* | 8/2018 | Uller | ............ | C12M 1/107 |

FOREIGN PATENT DOCUMENTS

| | | | | |
|---|---|---|---|---|
| KR | 10-1148194 B1 | 5/2012 | | |
| KR | 10-2016-0000123 A | 1/2016 | | |
| WO | WO-9322418 A1 * | 11/1993 | ............ | C02F 3/223 |

OTHER PUBLICATIONS

Yoo, Jae Jun, et al., "Development of thin-film photo-bioreactor and its application to outdoor culture of microalgae", *Bioprocess Biosyst Eng*, 2013, vol. 36, pp. 729-736 (8 pages in English).

Chinese Office Action dated Jul. 7, 2021 in counterpart Chinese Patent Application No. 201811136835.4 (7 pages in English and 8 pages in Chinese).

\* cited by examiner

Fig. 13A
Photosynthetic bioreactor with channel holes and 5 baffles
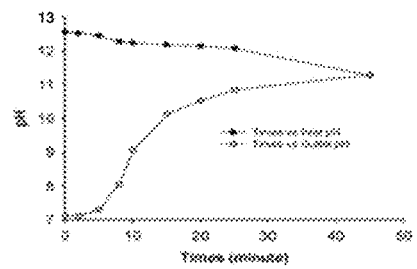
Photosynthetic bioreactor with 5 baffles
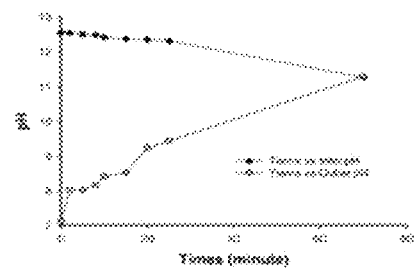
Photosynthetic bioreactor with channel holes and 6 baffles
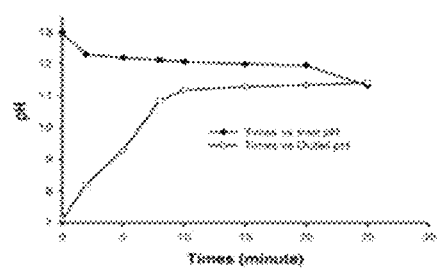
Photosynthetic bioreactor with 6 baffles
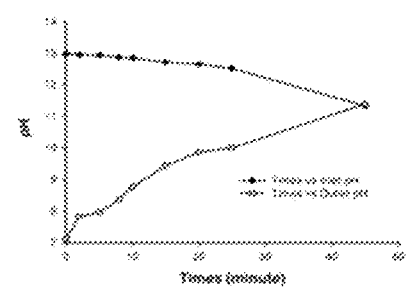
Fig. 13B
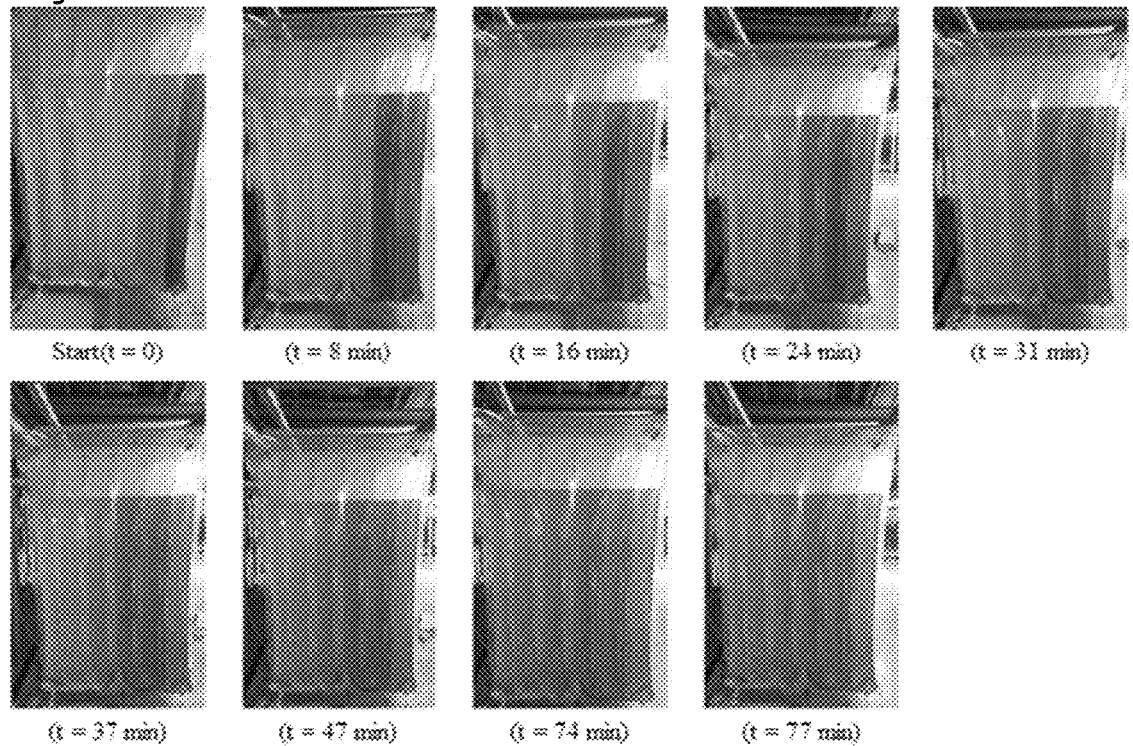

Fig. 14

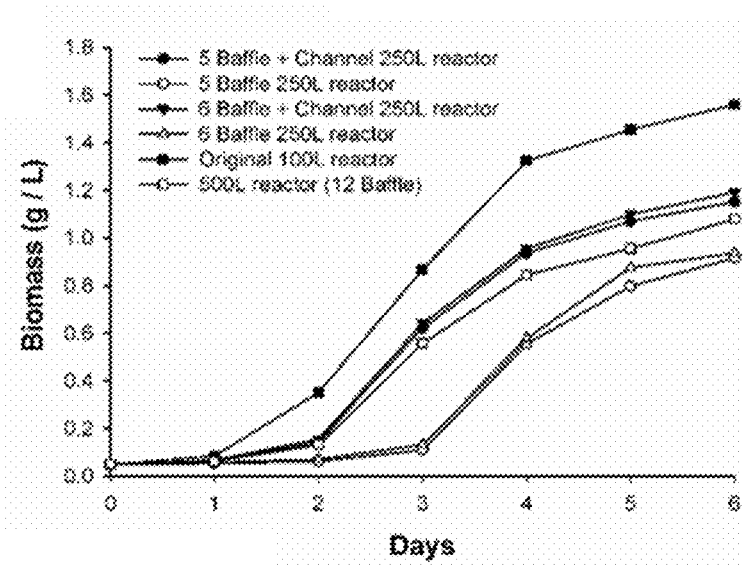

Fig. 15

(Reactor volume) x (number of reactors in tray) / (area of tray) x (amount of cells grown) = (degree of growth of cells per unit area)

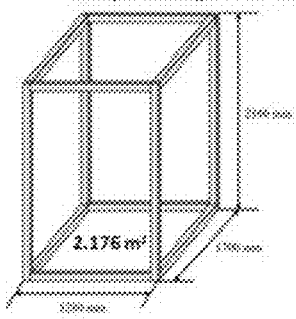

- General configuration having no baffle
  - 100 L reactor : (100 L x 3 / 2.176 m²) x 1.56 g/L = 215.06 g/m²
- Photosynthetic bioreactor including 6 baffles with channel holes (250 L)
  - 250 L reactor : (250 L x 3 / 2.176 m²) x 1.20 g/L = 413.60 g/m²
- Photosynthetic bioreactor including 14 baffles with channel holes (500 L)
  - 500 L reactor : (500 L x 3 / 4 m²) x 1.14 g/L = 427.5 g/m²

TRANSPARENT PHOTOBIOREACTOR FOR SCALE-UP CULTURE OF PHOTOSYNTHETIC ORGANISMS AND METHOD FOR FABRICATING THE SAME

CROSS REFERENCE TO RELATED APPLICATION(S)

This application claims the benefit under 35 USC 119(a) of Korean Patent Application Nos. 10-2017-0126877 filed on Sep. 29, 2017 and 10-2018-0094946 filed on Aug. 14, 2018 in the Korean Intellectual Property Office, the entire disclosure of which is incorporated herein by reference for all purposes.

TECHNICAL FIELD

The present invention relates to a large-scale photosynthetic bioreactor and a fabrication method thereof, and more particularly to a large-scale photosynthetic bioreactor in which transparent photobioreactors comprising a baffle are connected in parallel or in series by a adhesive element so that the reactor volume can be easily scaled up for scale-up culture of photosynthetic organisms, and to a fabrication method thereof.

BACKGROUND ART

The global warming caused by the emission of large amounts of greenhouse gases as a result of the use of fossil fuels threatens the survival of the organisms on the earth, including human beings. Accordingly, the development of carbon capture and sequestration (CCS) for the reduction of carbon dioxide is being actively carried out all over the world. The CCS technology is a method that captures high concentrations and large amounts of carbon dioxide emitted from various carbon emission sources, including thermal power plants, and then injects it into the ground or seabed to isolate them from the atmosphere. This CCS technology has the effect of reducing a large amount of carbon dioxide within a short period of time, but problems associated with stable storage, location selection and high installation costs are obstacles that block the realization of substantial CCS in Korea. Therefore, as a substitute for the CCS technology, Carbon Capture & Utilization (CCU) technology, which directly utilizes carbon dioxide for industrial purposes, but not storage purposes, or converts it into high value-added substances, is attracting attention, and the development of processes for converting carbon dioxide into various high value-added substances has also been attempted in Korea. Among these processes, a process for biologically converting carbon dioxide using microalgae, photosynthetic microorganisms, comes into the spotlight as an economical carbon dioxide reduction technology that can reduce carbon dioxide and, at the same time, produce various high value-added materials, including biofuels, bioplastics and pharmaceuticals.

Microalgae, called phytoplanktons, are photosynthetic underwater single-celled organisms, and are attracting attention as biomass resources having a very high potential to reduce greenhouse gases while producing energy and industrial materials, and the value of its future use in the fields of energy, chemicals and environment is expected to expand.

First, in the energy field, microalgae have the highest oil productivity among all biodiesel producing crops. Soybean, rape, sunflower, oil palm and the like are cultivated for 4 to 8 months, while microalgae are grown several times per day, and thus can be cultivated on a daily basis. In addition, microalgae have a high fat content per unit weight, so the annual oil production thereof is more than 100 times that of soybean. Further, microalgae are bio-resources free from the criticism that food resources are applied as energy, and these microalgae can produce biofuels having properties similar to those of petroleum diesel.

Second, in the chemical field, microalgae have the advantage of being able to produce various useful substances. These microalgae are currently industrialized mainly in the field of food, but will be industrialized in the biochemical and bioplastic fields in the future. Using *Chlorella*, *Spirulina* and *Chlamydomonas*, which are microalgae having high protein contents, as well as *Haematococcus* that produces the high value-added substance astaxanthin, functional health foods that supplement various amino acids, antioxidant substances and fatty acids have been commercialized.

Third, in the environmental field, microalgae are receiving the greatest attention in terms of enabling the reduction of carbon dioxide as described above, and related researches have been continuously conducted all over the world. Microalgae can absorb carbon dioxide in an amount equal to twice the biomass weight, and this absorption efficiency is 10 to 50 times higher than that of terrestrial plants. In addition, microalgae can be cultivated regardless of specific soil or water quality. Accordingly, related companies are increasingly trying to use microalgae for carbon dioxide reduction and plant wastewater purification.

The present inventors developed a photobioreactor made of a transparent film, which can achieve the purpose of effectively culturing microalgae (Korean Patent No. 10-1148194). However, the photobioreactor has a disadvantage in that the amount of microalgae that can be cultured is very small.

Small-scale microalgae cultivation has a limitation in that it cannot cope with a large amount of carbon dioxide emitted from large-scale industrial plants (coal-fired power plants, cogeneration plants, etc.). In order to overcome this limitation, a microalga culture system with a scale of several tons to several hundred tons is required. In the case of outdoor mass culture systems which are widely used worldwide, reinforced concrete structures are constructed to form pond type open culture facilities, or closed type photobioreactors using reinforced glass and acrylic are utilized. However, these microalgae culture systems have a drawback in that as the culture size increases, the initial investment cost and the maintenance cost also significantly increase. In addition, conventional photobioreactors made of a vinyl material have a shortcoming in that the risk of leakage and breakage increases as the volume of culture medium in the reactor increases, due to the limitation of the structure.

Under this background, the present inventors have made extensive efforts to develop a photosynthetic bioreactor enabling the large-scale culture of photosynthetic microorganisms, and as a result, have found that when a photosynthetic bioreactor is fabricated by minimizing the bonding area of the reactor and introducing a straight line-type sparger, a adhesive element, an annular support structure and a baffle, carbon dioxide and photosynthetic organisms in the reactor can be more distributed, and the reduction in light transmittance caused by a deformation in the reactor shape can be prevented, thereby completing the present invention.

DISCLOSURE OF INVENTION

Technical Problem

It is an object of the present invention to provide a large-scale photosynthetic bioreactor whose volume can be easily scaled up for scale-up culture of photosynthetic organisms, and to a fabrication method thereof.

Technical Solution

To achieve the above object, the present invention provides a large-scale photosynthetic bioreactor comprising multiple photosynthetic bioreactor unit of which each is connected in series or in parallel 9*by an adhesive unit, the photosynthetic bioreactor unit comprising: (a) a culture vessel in which the photosynthesis of photosynthetic organisms occurs; (b) a multi-purpose inlet/outlet unit formed at the outer lower end of the culture vessel; (c) an external tube disposed outside the culture vessel and connected to the multi-purpose inlet/outlet unit; (d) an internal tube disposed inside the culture vessel and connected to the multi-purpose inlet/outlet unit; and (e) one or more baffles disposed in the culture vessel, wherein the baffle has one to five channel holes formed on the surface thereof, and the culture vessel is made of a transparent film.

The present invention also provides a method for fabricating a large-scale photosynthetic bioreactor, comprising the steps of: (a) forming a hole for attachment of a multi-purpose inlet/outlet unit at a lower end of a culture vessel; (b) attaching one or more baffles to the inside of the culture vessel; (c) installing the multi-purpose inlet/outlet unit, an internal tube and an external tube in the culture vessel; (d) connecting individual photosynthetic bioreactors to each other by an adhesive unit; and (e) supporting the top and bottom of the reactors by a support to arrange them in a vertical form.

Advantageous Effects

The large-scale photosynthetic bioreactor according to the present invention makes it possible to culture a larger amount of microalgae than a conventional photobioreactor in the same area. In addition, it has high light transmittance, produces a large amount of biomass per unit area due to smooth mixing, and has a significant effect of reducing carbon dioxide. Furthermore, the present invention has an advantage in that the number of photosynthetic bioreactors required to culture the same scale of photosynthetic organisms is significantly smaller than that in a conventional process for culture of photosynthetic organisms, thereby reducing the time spent to fabricate the reactor and thus increasing space utilization per unit area to improve efficiencies in an economic respect including rental costs. In conclusion, the development of a transparent photosynthetic bioreactor whose volume can be easily scaled up for scale-up culture of photosynthetic organisms enables mass-production and sale of drugs, functional foods, cosmetics, feedstuffs and the like by a low-cost, high-efficiency microalgae-based biomass production along with the achievement of the purpose of reducing a large amount of carbon dioxide.

BRIEF DESCRIPTION OF THE DRAWINGS

The patent or application file contains a least one drawing executed in color. Copies of this patent or patent application publication with color drawing(s) will be provided by the Office upon request and payment of the necessary fee.

FIG. 13A is a graph comparing the efficiency of mixing according to the number of baffles and the presence or absence of channel holes, and FIG. 13B depicts photographs showing the results of observing the migration of microalgae at various time points.

FIG. 14 is a graph comparing the degree of growth of *Chlorella vulgaris* between a conventional photobioreactor made of vinyl and designed photobioreactors (in the case of the designed photobioreactors, comparison was made between 250 L and 500 L reactors, which had 5 or 6 baffles or had no baffle).

FIG. 15 shows the production of biomass per unit area of designed photosynthetic bioreactors.

BEST MODE FOR CARRYING OUT THE INVENTION

Figure 1A:
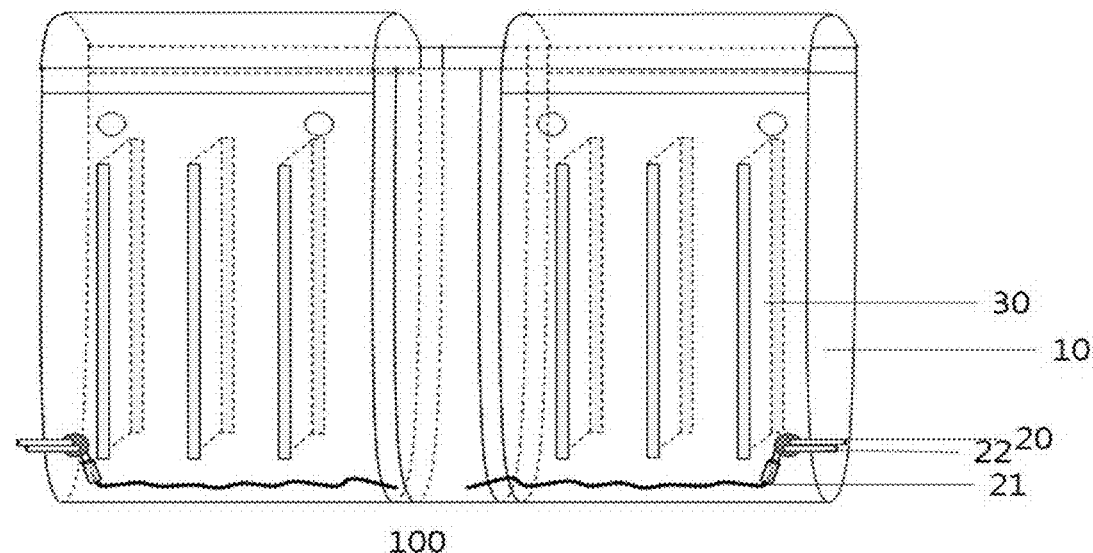
FIG. 1A is a schematic perspective view of a large-scale photosynthetic bioreactor for scale-up culture of photosynthetic organisms.

While the invention can be modified in various ways and take on various alternative forms, specific embodiments thereof are shown in the drawings and will be described in detail below as examples. It should be understood, however, that there is no intent to limit the invention to the particular forms disclosed, but on the contrary, the invention is to cover all modifications, equivalents, and alternatives falling within the spirit and scope of the appended claims.

It will be understood that, although the terms "first", "second", "A", "B", etc. may be used herein to describe various elements of the invention, these elements should not be limited by these terms. The terms are used only to distinguish an element from another. For example, a first element could be termed a second element, and, similarly, a second element could be termed a first element, without departing from the scope of the present invention. As used herein, the term "and/or" includes any and all combinations of one or more of the associated listed items.

As used herein, the singular forms "a," "an" and "the" are intended to include the plural forms as well, unless the context clearly indicates otherwise. It will be further understood that the terms "comprises," "comprising," "includes," and/or "including," when used herein, specify the presence of stated features, numbers, steps, operations, elements, components, and/or combinations thereof but do not preclude the presence or addition of one or more other features, numbers, steps, operations, elements, components, and/or combinations thereof.

Before starting detailed explanations of figures, components that will be described in the specification are discriminated merely according to functions mainly performed by the components or conventionally carried out according to common knowledge of related technical fields. That is, two or more components which will be described later can be integrated into a single component. Furthermore, a single component which will be described later can be separated into two or more components. Moreover, each component which will be described can additionally perform some or all of a function executed by another component in addition to the main function thereof. Some or all of the main function of each component which will be described can be carried out by another component.

Also, in the execution of a method or an operation method, unless the context clearly indicates a specific order, steps constituting the method may be executed differently from the specified order. That is, the steps may be executed in the same order as specified, may be executed substantially concurrently, or may be executed in a reverse order.

In the present invention, the efficiency of large-scale culture in a large-scale photosynthetic bioreactor whose volume can be easily scaled up for scale-up culture of photosynthetic organisms was examined.

In the present invention, microalgae were cultured in a photosynthetic bioreactor comprising a culture vessel made of a transparent film and a baffle and in a control, and as a result, it could be seen that, in the designed photosynthetic bioreactor, culture of a large amount of microalgae was smoothly achieved in the same area, and the biomass productivity was also high.

In other words, in one example of the present invention, photosynthetic bioreactors were fabricated, each of which includes a culture vessel made of a film formed from a mixture of low-density polyethylene (LDPE) film, polyethylene terephthalate (PET) and nylon 8. Then, the bioreactors were connected to each other by an adhesive element, thereby fabricating a large-scale photosynthetic bioreactor, and the microalga *Chlorella vulgaris* was cultured therein. As a result, it could be seen that the culture vessel had high light transmittance and could achieve scale-up culture.

Therefore, in one aspect, the present invention is directed to a photosynthetic bioreactor comprising: (a) a culture vessel in which the photosynthesis of photosynthetic organisms occurs; (b) a multi-purpose inlet/outlet unit formed at the outer lower end of the culture vessel; (c) an external tube disposed outside the culture vessel and connected to the multi-purpose inlet/outlet unit; (d) an internal tube disposed inside the culture vessel and connected to the multi-purpose inlet/outlet unit; and (e) one or more baffles disposed in the culture vessel, wherein the culture vessel is made of a transparent film.

Hereinafter, a photosynthetic bioreactor according to the present invention will be described in detail.

FIG. 1A is a schematic perspective view showing a structure of a photosynthetic bioreactor 100 according to one embodiment of the present invention.

As shown in FIG. 1A, the culture vessel 10 is made of a transparent film. The transparent film can be used without being particularly limited as long as it is transparent to facilitate the growth of photosynthetic organisms and is high in light transmittance. Examples of the transparent film may include a low-density polyethylene (LDPE) film, a film formed from a mixture of polyethylene terephthalate (PET) and casting polypropylene (PET+CPP), a polyacetal (POM) film, a polycarbonate (PC) film, a polyester sulfon (PES) film, a polyethylene (PE) film, a polyvinyl chloride (PVC) film, a polyethylene terephthalate (PET) film, a polypropylene (PP) film, a polyphenylene oxide (PPO=PPE) film, and a film formed from a mixture of low-density polyethylene, polyethylene terephthalate and nylon 8. The transparent film has an advantage in that it is lightweight, transparent, and high in mechanical strength while having a light transmittance equivalent to those of glass, acryl and the like, which are widely used as a material for the culture vessel of the photosynthetic bioreactor.

A culture vessel 10 constituting the photosynthetic bioreactor according to the present invention is characterized in that it has a plate type and a bubble column type when medium is injected therein. Since the culture vessel is of a plate type, the distance inside the reactor through which light is transmitted is shortened, and thus the light transmittance is high.

The photosynthetic microorganisms injected into the culture vessel 10 are roughly classified into microalgae, cyanobacteria, and photosynthetic bacteria.

As used herein, the term "microalgae" refers to single-celled (or unicellular) eukaryotic microorganisms that photosynthesize with photosynthetic pigments.

Examples of the microalgae include *Anacystis nidulans, Ankistrodesmus* sp., *Biddulpha aurita, Botryococcus braunii, Chaetoceros* sp., *Chlamydomonas applanata, Chlamydomonas reinhardtii, Chlorella* sp., *Chlorella ellipsoidea, Chlorella emersonii, Chlorella protothecoides, Chlorella pyrenoidosa, Chlorella sorokiniana, Chlorella vulgaris, Chlorella minutissima, Chlorococcus littorale, Cyclotella cryptica, Dunaliella bardawil, Dunaliella salina, Dunaliella tertiolecta, Dunaliella primolecta, Gymnodinum* sp., *Hymenomonas carterae, Isochrysis galbana), Isochrysis* sp., *Microcystis aeruginosa, Micromonas pusilla, Monodus subterraneous, Nannochloris* sp., *Nannochloropsis* sp., *Nannochloropsis atomus, Nannochloropsis salina, Navicula pelliculosa, Nitzschia* sp., *Nitzscia closterium, Nitzscia palea, Oocystis polymorpha, Ourococcus* sp., *Oscillatoria rubescens, Pavlova lutheri, Phaeodactylum tricornutum, Pycnococcus provasolii, Pyramimonas cordata, Spirulina platensis, Stephanodiscus minutulus, Stichococcus* sp., *Synedra ulna, Scenedesmus obliquus, Selenastrum gracile, Skeletonoma costalum, Tetraselmis chui, Tetraselmis maculata, Tetraselmis* sp., *Tetraselmis suecica, Thalassiosira*

*pseudomona*, and the like. In the present invention, one or more selected from the above-enumerated group of such microalgae may be used.

As used herein, the term "cyanobacteria" refers to bacteria that photosynthesize using chlorophyll among prokaryotes.

Examples of the cyanobacteria include *Anabaena* sp., *Calothrix* sp., *Chaemisiphon* sp., *Chroococcidiopsis* sp., *Cyanothece* sp., *Cylindrospermum* sp., *Dermocarpella* sp., *Fischerella* sp., *Gloeocapsa* sp., *Myxosarcina* sp., *Nostoc* sp., *Oscillatoria* sp., *Phormidium corium, Pleurocapsa* sp., *Prochlorococcus* sp., *Pseudanabaena* sp., *Synechococcus* sp., *Synechocystis* sp., *Tolypothrix* sp., *Xenococcus* sp., and *the* like. In the present invention, one or more selected from the above-enumerated group of such cyanobacteria may be used.

As used herein, the term "photosynthetic bacteria" refers to bacteria that perform carbon dioxide assimilation using light energy.

Examples of the photosynthetic bacteria include *Rhodocista centenaria, Rhodospira trueperi, Rhodospirillum fulvum, Rhodospirillum molischianum, Rhodospirillum photometricum, Rhodospirillum rubrum, Rhodospirillum salexigens, Rhodospirillum salinarutn, Rhodospirillum sodomense, Rhodospirillum mediosalinum, Rhodopseudomonas* sp., *Rhodpseudomonas acidophila, Rhodopseudomonas capsulatus, Rhodopseudomonas palustris, Rhodopseudomonas sphaeroides, Rhodobacter capsulatus, Rhodobacter sphaeroides*, and the like. In the present invention, one or more selected from the above-enumerated group of such photosynthetic bacteria may be used.

These photosynthetic bacteria have bacteriochlorophyll instead of chlorophyll, and thus they can be grown by photosynthesis using carbon dioxide as a material.

Figure 3:
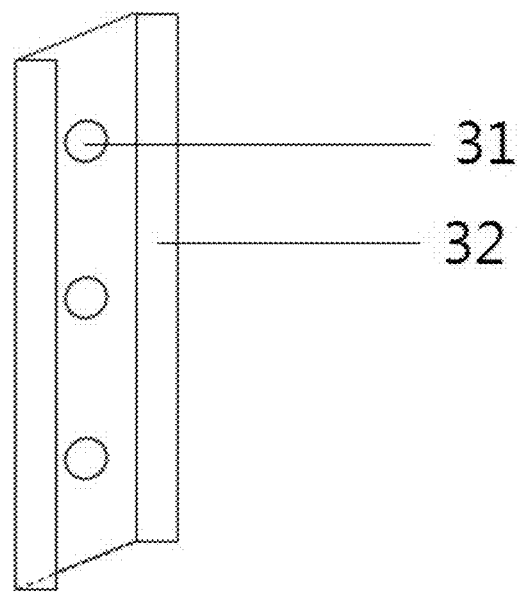
FIG. 3 is a schematic perspective view of a baffle in which channel holes are formed for effective mixing of culture medium in a column in a reactor.

FIG. 3 is a schematic view showing a baffle according to one embodiment of the present invention. As shown in FIG. 3, the baffle of the present invention may have a number of channel holes 31 formed at the longitudinal center thereof and may be used to partially partition the inside of a culture vessel 10 to increase the culture volume. In the case of a reactor having no baffle, five thermal bonding surfaces (where the total number of columns is 6) occurs, but in the case of a reactor having a baffle, 10 thermal bonding surfaces occurs, resulting in an increase in volumetric capacity. Moreover, a portion 32 of the baffle of the present invention, which is bonded to the culture vessel, may be made of polyethylene in order to easily achieve its thermal bonding to the culture vessel.

Figure 16:
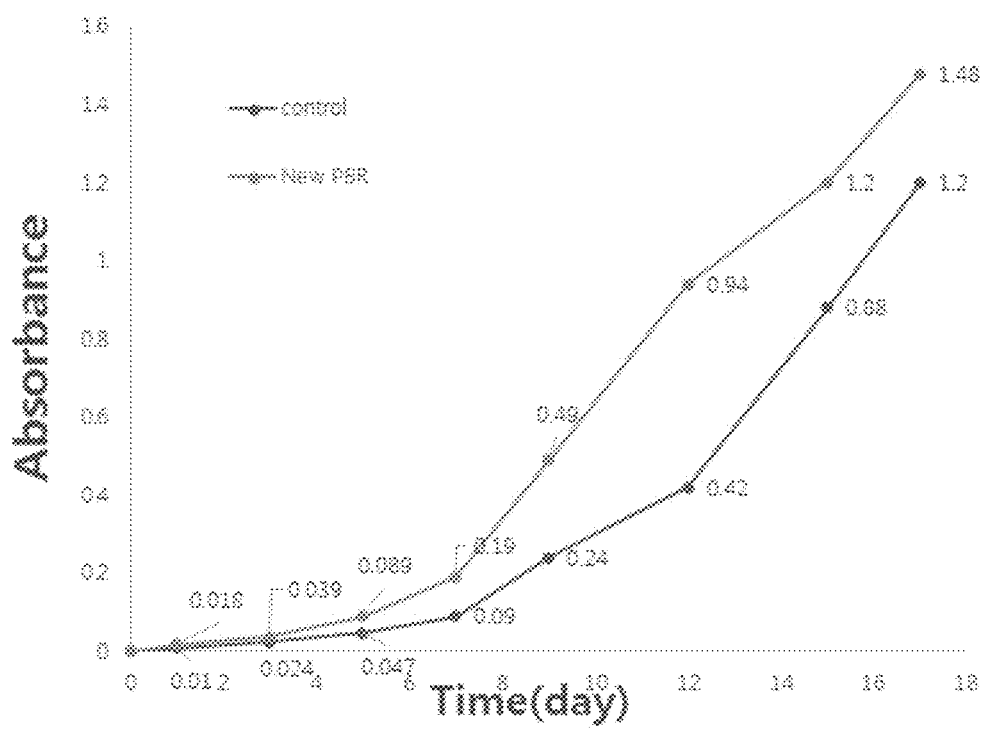
FIG. 16 is a graph comparing the degree of growth of *Chlorella vulgaris* between a conventional photobioreactor made of vinyl and a designed photobioreactor (control: the conventional photobioreactor made of vinyl; and New PBR: the designed photobioreactor).
Figure 17:
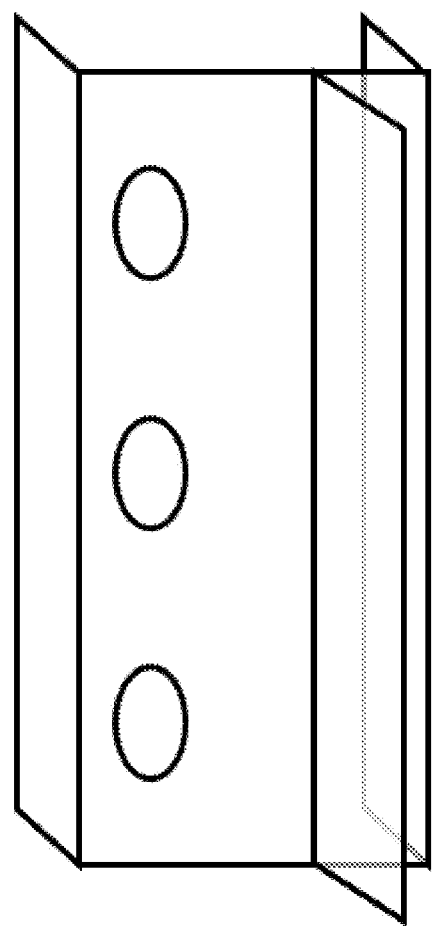
FIG. 17 is a schematic view of an anchor-type baffle comprising an impeller.

The baffle may be of a plate type like the culture vessel, but is not limited thereto. For example, as shown in FIG. 16, the baffle may be an anchor-type baffle comprising an impeller additionally mounted to the rear end thereof.

The impeller of the anchor-type baffle can fragment air discharged from the sparger to increase the air surface area and thus the air transfer efficiency, thereby increasing the culture efficiency.

Figure 1B:
FIG. 1B is a photograph of an actually fabricated photosynthetic bioreactor.

As shown in FIGS. 1A and 1B, the internal space of the culture vessel 10 is characterized in that it is partially partitioned because a predetermined portion thereof is partitioned by a baffle bonded to the inner side of the front and rear sides of the culture vessel. Since the culture vessel 10 is made of a transparent film, it can be partitioned when a baffle is bonded thereto.

In the present invention, the expression "internal space is partially partitioned" means that the internal space of the culture vessel is vertically partitioned. Here, the partition does not extend from the top end to the bottom end of the culture vessel, but is spaced at a distance from the top and bottom ends of the culture vessel. Thus, medium in the culture vessel can move through flow paths provided by the spacing.

The partition may be formed between the multi-purpose inlet/outlet unit and the top of the culture vessel. The length of the partition may vary depending on the height of the reactor. If the length of the partition, i.e., the baffle, is excessively short, the effect of the partition cannot be obtained, and if the length of the partition is excessively long, the uniform distribution of carbon dioxide and photosynthetic organisms in the internal space of the reactor can become difficult.

The distance between the partitions, that is, the distance between one baffle and the next baffle, can be suitably selected without particular limitation depending on the volume of the reactor and the like as described above.

Figure 4:
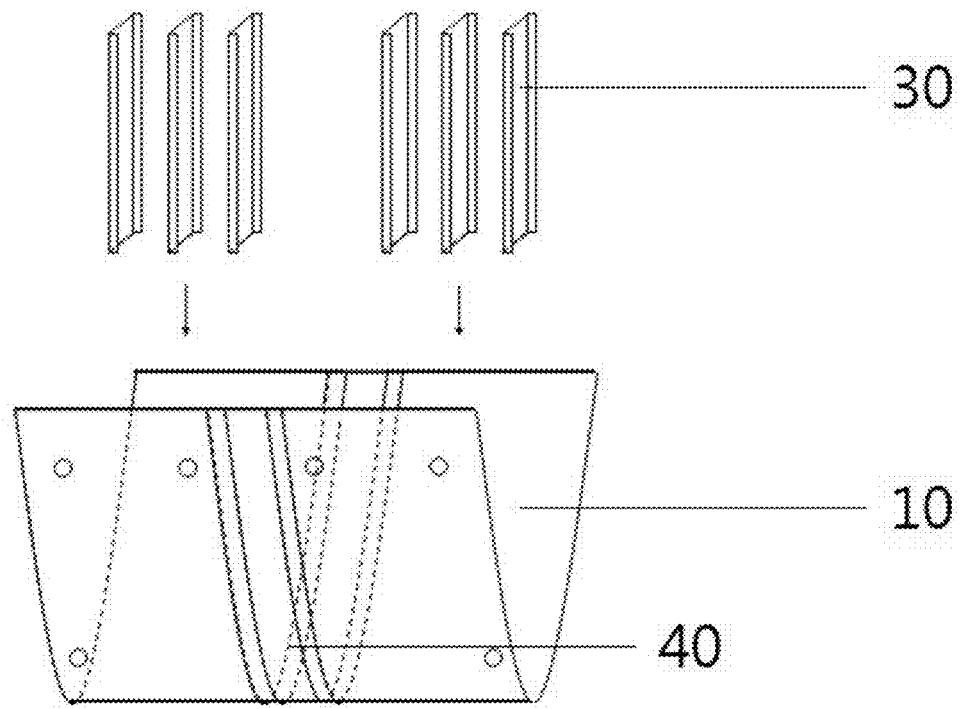
FIG. 4 is a schematic perspective view showing that baffles fabricated in order to inject an increased amount of culture medium into a column in a reactor are connected to the reactor.

FIG. 4 depicts a method of arranging baffles when fabricating a large-scale photosynthetic bioreactor according to one embodiment of the present invention. As shown in FIG. 4, one or more baffles may be incorporated in the culture vessel. When n reactor modules are connected to each other, m (m>7) baffles may be bonded to the reactors in a number of mn, mn−1, mn−2, or mn−3.

Figure 5:
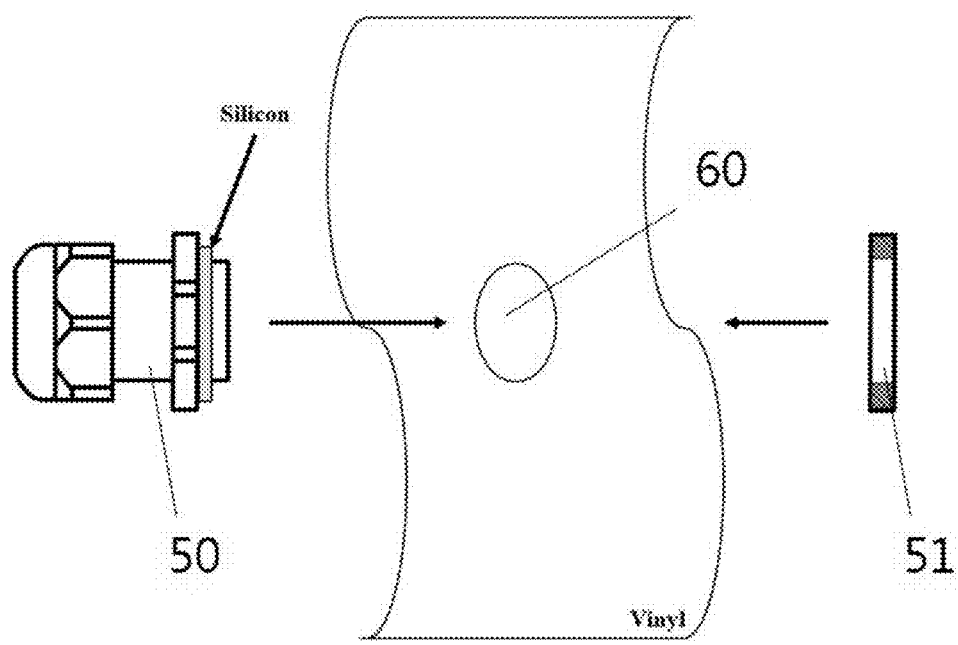
FIG. 5 is a schematic view showing that an adaptor into which a rubber stopper having gas injection and sampling tubes coupled thereto can be inserted is fixed to a film type reactor using silicon.

FIG. 5 illustrates the coupling of a fixing/connection element to the multi-purpose inlet/outlet unit according to one embodiment of the present invention. The multi-purpose inlet/outlet unit 20 is detachably coupled to the outer lower end of the culture vessel 10. As shown in FIG. 5, a fixing/connection element 50 located inside and outside the culture vessel 10 is composed of a fixing/connection element located outside the culture vessel and a fitting nut 51 located inside the culture vessel. The multi-purpose inlet/outlet unit may be attached through a hole 60 of the reactor, and the hole may be adjusted depending on the size of the inlet/outlet unit.

Figure 6:
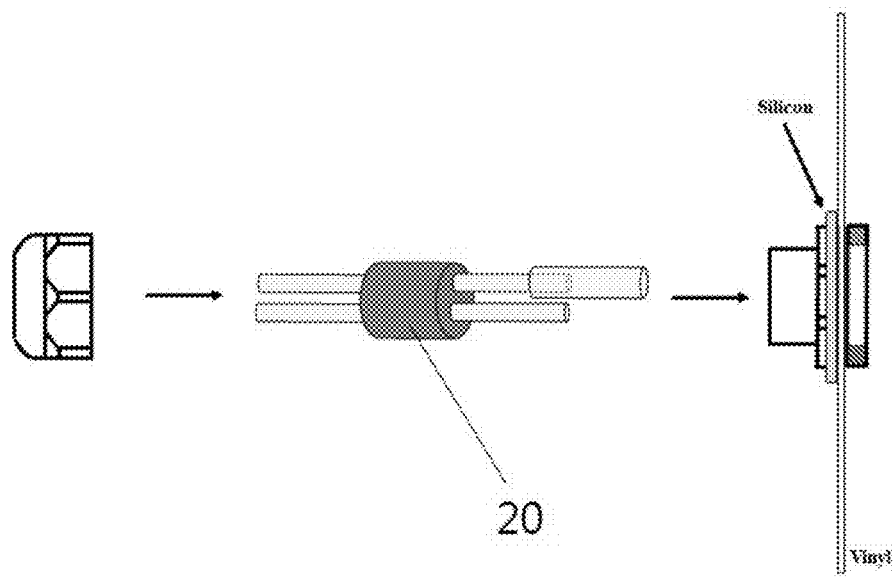
FIG. 6 is a schematic view showing a process in which a rubber stopper having gas injection and sampling tubes coupled thereto is inserted into an adaptor fixed to a reactor and the periphery of the adaptor is covered with silicon in order to leakage.

FIG. 6 shows an example of coupling the multi-purpose inlet/outlet unit according to one embodiment of the present invention. As shown in the figure, the multi-purpose inlet/outlet unit may be attached after opening the stopper of the fixing/connection element, and the fixing/connection element may be treated with silicon in order to prevent leakage.

The multi-purpose inlet/outlet unit 20 may be connected with a tube for performing a function selected from the group consisting of (a) injecting photosynthetic organisms and culture medium, (b) injecting a carbon dioxide-containing gas, (c) extracting a sample, and (d) discharging gases. The number of the tubes may be set without being particularly limited.

Figure 7:
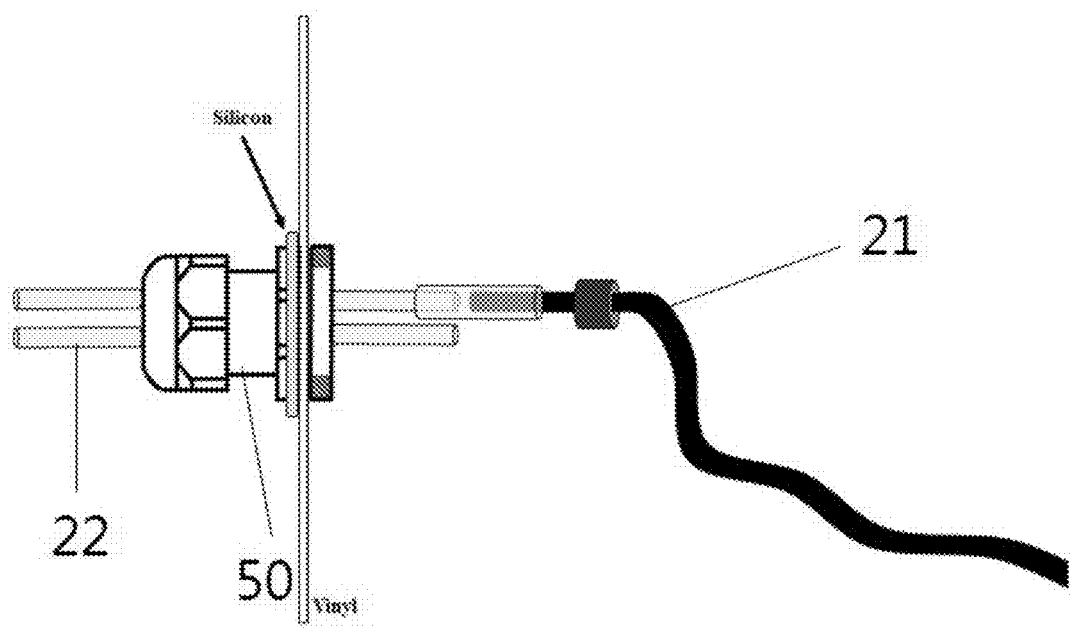
FIG. 7 is a schematic view showing a process of connecting a straight line type sparger to a fixed rubber stopper so as to prevent leakage occurrence.

FIG. 7 is a schematic view showing a multi-purpose inlet/outlet unit installed at a photosynthetic bioreactor according to one embodiment of the present invention. As shown in FIG. 7, the multi-purpose inlet/outlet unit is connected with an external tube 22 disposed outside the culture vessel and an internal tube 21 disposed inside the culture vessel and connected to the multi-purpose inlet/outlet unit.

In the present invention, the external tube and the internal tube can be used without being particularly limited as long as they are formed in a hollow hose shape, but a sterilizable hose made of stainless steel, silicon or the like is preferably used. In addition, the external tube and the internal tube may be formed integrally with each other, or may be connected to the multi-purpose inlet/outlet unit 20, respectively.

In the present invention, the internal tube may be a four-way sparger.

The external tube 22 for introducing the carbon dioxide-containing gas, connected to a hole for introducing the carbon dioxide-containing gas, is configured to supply carbon dioxide into the photosynthetic bioreactor 100. In this case, the amount of the carbon dioxide being supplied can be controlled through a flow meter separately provided at the outside of the photosynthetic bioreactor. The distribution of carbon dioxide may vary depending on the size or characteristics of photosynthetic organisms in the photosynthetic bioreactor 100, the internal size of the reactor, or the properties of an injector. Thus, the supply amount of carbon dioxide is preferably controlled by using the flow meter.

The number of the multi-purpose inlet/outlet units 20 may be determined optionally depending on the volume of the reactor 100.

Figure 8:
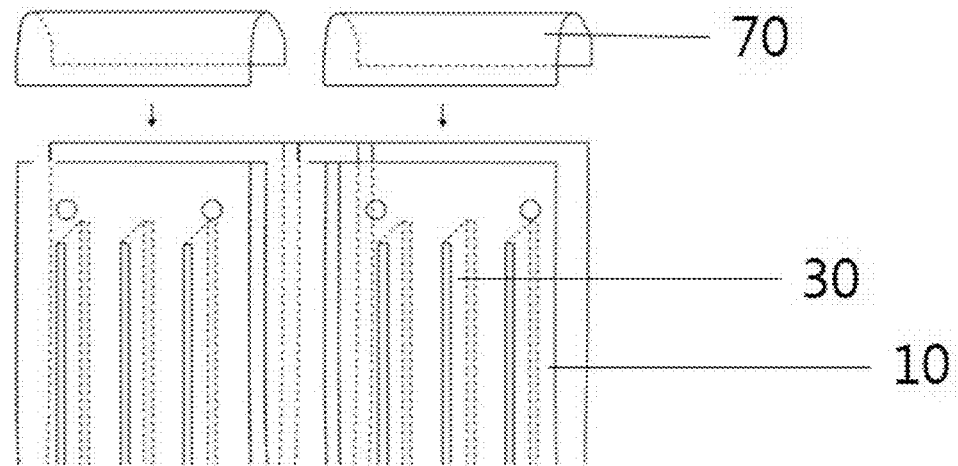
FIG. 8 is a schematic perspective view showing a process in which annular supports are connected to the upper end of a reactor comprising baffles and adhesive elements so that they can be hang on a tray.
Figure 9:
FIG. 9 shows the actual appearance of a structure configured such that the support of a tray can more stably withstand the load of a reactor.

FIG. 8 shows a process in which annular supports 70 are connected to the upper end of a large-scale photosynthetic reactor comprising baffles and adhesive elements so that they can be attached so as to be hang on a tray, and FIG. 9 shows the actual photographs of the annular support that is installed.

Figure 10:
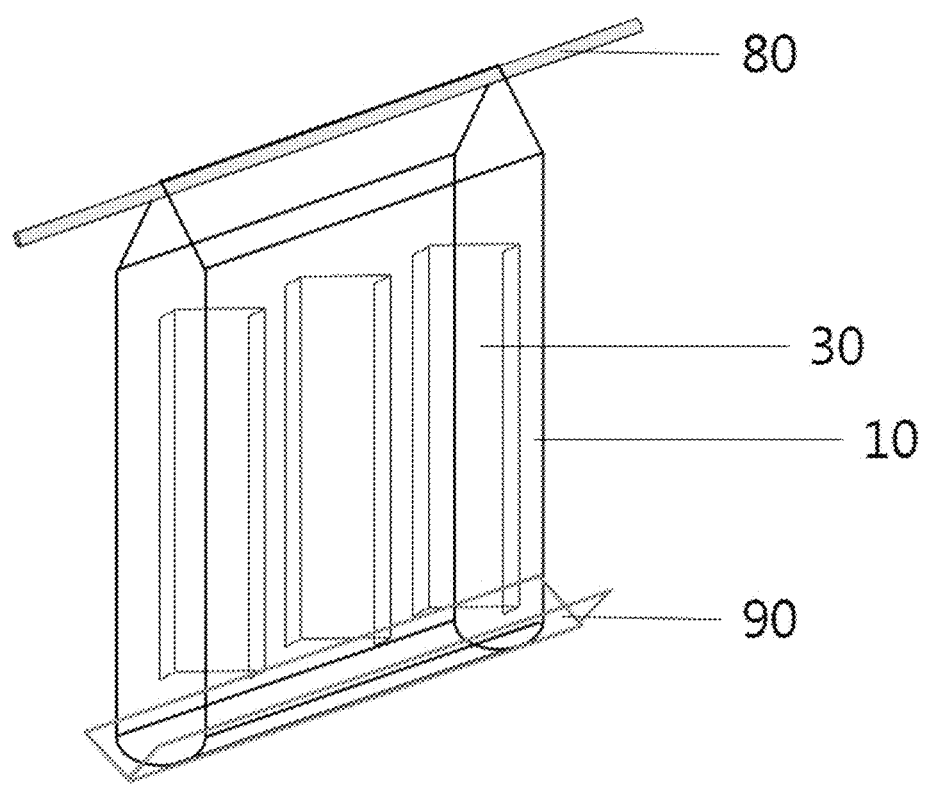
FIG. 10 is a schematic perspective view showing that a support is disposed on the lower end of a reactor in order to provide stability.

FIG. 10 is a schematic view showing that a support rod 80 connected to the support 70 is formed at the top end of the culture vessel 10 and a support 90 is disposed at the bottom end so that the photosynthetic bioreactor according to one embodiment of the present invention can be supported or fixed. The support 70 is hollow such that the support rod 80 may be inserted therein. Both ends of the support rod 80 may be mounted on a separate stand or the like.

The vertical length or height of the photosynthetic bioreactor 100 according to the present invention is 20 to 500 cm, preferably, 40 to 200 cm, the horizontal length thereof is preferably 3 to 1500 cm, and the lateral length (or thickness) thereof is preferably 2 to 50 cm. The lateral length of the photosynthetic bioreactor means the thickness of the photosynthetic bioreactor, measured when culture medium is introduced into the photosynthetic bioreactor.

The height of the baffle according to the present invention may be 15 to 400 cm, preferably 30 to 200 cm, and the horizontal length thereof may be 10 to 20 cm, and the diameter of the channel hole 31 thereof may be 1 to 5 cm.

In another aspect, the present invention is directed to a large-scale photosynthetic bioreactor comprising multiple photosynthetic bioreactor unit of which each is connected in series or in parallel by an adhesive unit, the photosynthetic bioreactor unit comprising: (a) a culture vessel in which the photosynthesis of photosynthetic organisms occurs; (b) a multi-purpose inlet/outlet unit formed at the outer lower end of the culture vessel; (c) an external tube disposed outside the culture vessel and connected to the multi-purpose inlet/outlet unit; (d) an internal tube disposed inside the culture vessel and connected to the multi-purpose inlet/outlet unit; and (e) one or more baffles disposed in the culture vessel, wherein the baffle has one to five channel holes formed on the surface thereof, and the culture vessel is made of a transparent film.

Figure 2:
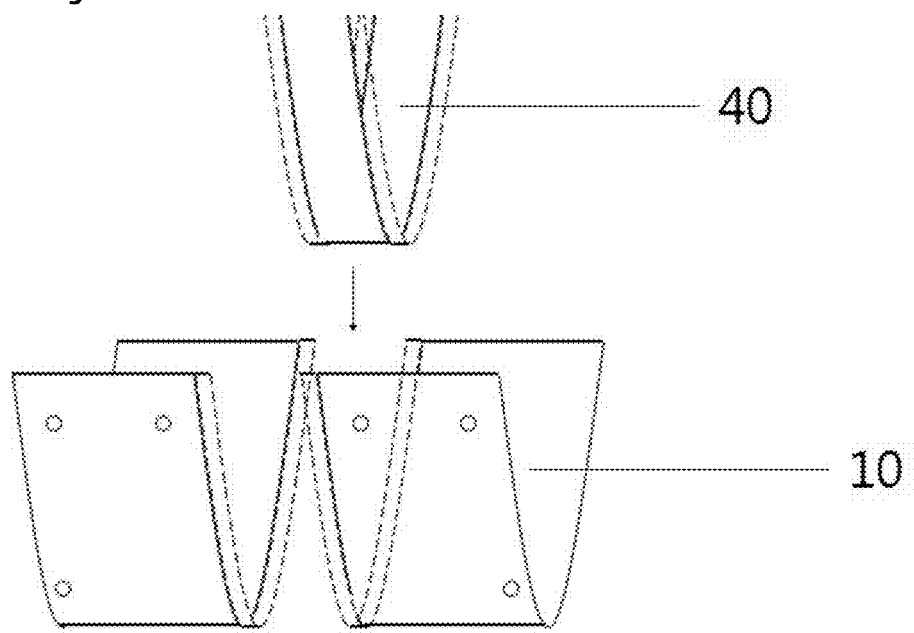
FIG. 2 is a schematic perspective view showing that an adhesive element fabricated for connection between single reactors for scaling up was bonded to each single reactor.

FIG. 2 shows a process of connecting an adhesive element to two adjacent culture vessels of the photosynthetic bioreactor according to one embodiment of the present invention. The adhesive element of present invention may be made of transparent film while both side ends of the adhesive element 40 may be made of a polyethylene material so that both confronting side ends of the two adjacent culture vessels of the photosynthetic bioreactor are connected to each other by thermal bonding.

In the present invention, the large-scale photobioreactor may be configured to culture photosynthetic microorganisms with 500 to 1000 L of culture medium.

In the present invention, the adhesive unit may be square shape, the height of the adhesive element is preferably twice that of the photosynthetic bioreactor, and the horizontal length thereof may be 10 to 20 cm.

The present invention also provides a method for fabricating a large-scale photosynthetic bioreactor, comprising the steps of:

(a) forming a hole for attachment of a multi-purpose inlet/outlet unit at a lower end of a culture vessel;

(b) attaching one or more baffles to the inside of the culture vessel;

(c) installing the multi-purpose inlet/outlet unit, an internal tube and an external tube in the culture vessel;

(d) connecting individual photosynthetic bioreactors to each other by an adhesive unit; and (e) supporting the top and bottom of the reactors by a support to arrange them in a vertical form.

In the present invention, the hole in step (a) may be formed by directing perforating the culture vessel.

In the present invention, the baffle in step (b) may be securely fixed to the culture vessel by a water-soluble adhesive, and then attached to the culture vessel by thermal bonding.

In the present invention, the water-soluble adhesive can be used without being particularly limited as long as it is any adhesive that reacts with water and is dissolved in water, but it may preferably be a water-based paste.

In the present invention, the step of installing the multi-purpose inlet/outlet unit may comprise filling silicon between the culture vessel and the multi-purpose inlet/outlet unit.

In the present invention, the dead zone of the both-end column of the photosynthetic bioreactor, in which microalgae accumulate due to non-flowability, may be removed, and both lower ends of the reactors may be thermally bonded in an oblique direction in order to reduce applied pressure.

In the present invention, step (d) may comprise connecting both sides of the individual photosynthetic bioreactors with adhesive elements by thermal bonding.

In the present invention, the method for fabricating a large-scale photosynthetic bioreactor may further comprise a step of installing an auxiliary support at the lower end of the large-scale photosynthetic bioreactor.

EXAMPLES

Hereinafter, the present invention will be described in further detail with reference to examples. It will be obvious to a person having ordinary skill in the art that these examples are for illustrative purposes only and are not to be construed to limit the scope of the present invention.

In particular, the culture was performed on *Chlorella vulgaris* among microalgae in the photosynthetic bioreactor according to the present invention in the following examples. However, it will be obvious to those skilled in the art that other kinds of microalgae may also be cultured.

Example 1. Process for Fabrication of Constituent Elements Including Photosynthetic Bioreactor Using low-density polyethylene film (LDPE), polyethylene terephthalate (PET) and nylon 8, which were wound in a roll form, a photosynthetic bioreactor (height: 180 cm, horizontal length: 120 cm, lateral length: 21 cm, and volume: 200 L or more), an adhesive portion (height: 400 cm, and horizontal length: 12 cm) and a baffle (height: 160 cm, and horizontal length: 16 cm) were fabricated (FIGS. 1A and 1B).

Example 2. Detailed Process for Fabrication of Constituent Elements

At the left and right lower ends of a photosynthetic bioreactor to which elements were not connected, 3-cm-diameter holes for sampling including gas injection were made using a compass. adhesive elements fabricated for connection between single photosynthetic bioreactors were located at both ends of each of the single reactors which were then connected to each other using a thermal bonding machine. At this time, it was shown that the lower end of the connected photosynthetic bioreactors had a "U" shape when viewed from the side.

For effective mixing of medium contained in the column in the reactor, three channel holes, each having a diameter of 2 cm, were made in each baffle by use of a compass. The baffles were connected to the reactors, connected by the adhesive elements, by use of a thermal bonding device. When reactor modules were connected to one another, m (m>7) baffles may be bonded to the reactors in a number of mn, mn−1, mn−2, or mn−3.

Thereafter, the periphery of an adaptor was covered with silicon in order to prevent leakage from the hole formed at the lower end (FIGS. 5 and 7), and a straight line-type gas injector (sparger) and a sampling) line were connected to the adaptor. A hose tightener was disposed around the end of the sampling line in order to prevent leakage.

The top, bottom, left and right sides of the photosynthetic bioreactors were connected to one another by use of a thermal bonding device, and an annular support was additionally bonded to the upper end of the photosynthetic bioreactor (FIGS. 8 and 9).

Figure 11:
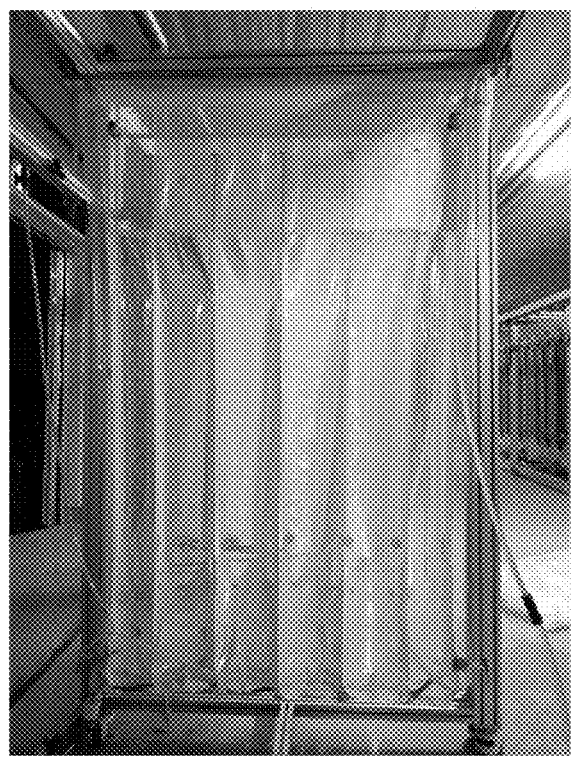
FIG. 11 shows that water is actually filled into a reactor through a tube.
Figure 12:
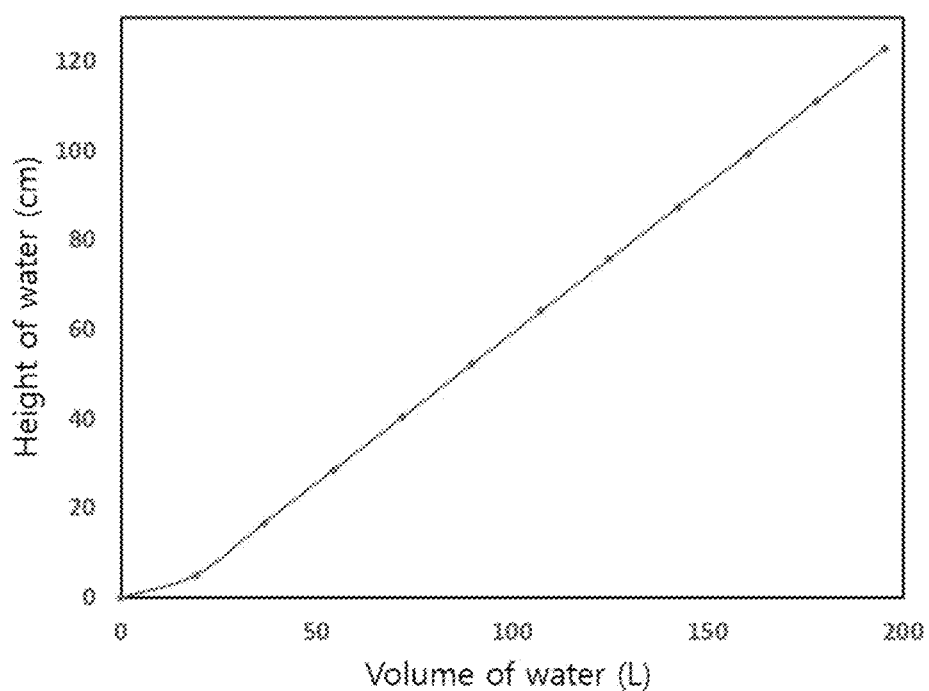
FIG. 12 is a graph showing the relationship between the amount of water filled into a reactor and the height of the water in the reactor.

The dead zone of the both-end column of the reactor was removed, and both lower ends of the reactors were thermally bonded in an oblique direction in order to reduce applied pressure, thereby fabricating a photosynthetic bioreactor (FIGS. 10 and 11).

The outer portion of the photosynthetic reactor was made of PE, PET and nylon, and thus the adhesive element could not be thermally bonded thereto. For this reason, the photosynthetic bioreactor was fabricated in the form of a diaper and bonded to the bioreactor (FIG. 2).

Example 3. Examination of the Microalga Culture Ability of Large-Scale Photosynthetic Bioreactor In order to prevent the support in the tray from being deformed due to the load that increased as medium was filled in the photobioreactor, an auxiliary support was installed in the middle of the support as shown in FIG. 9.

A photosynthetic bioreactor comprising was hang on the support of a tray. Then, a gas tube for injecting an air containing 3-5% carbon dioxide was connected to the gas inlet, after which water, culture medium and *Chlorella vulgaris* were sequentially injected into the reactors through the tube, followed by culture.

TAP-C (consisting of 0.5M TRIS base, nutrient stock, phosphate buffer, Kutner, and HCl) was used as medium, and culture was performed for 18 days.

As a result, it could be seen that the degree of cell growth in the photosynthetic bioreactor fabricated in the present invention was much higher than that in a photobioreactor (control) fabricated in a previous invention (Korean Patent No. 10-1148194) (FIG. 16).

Example 4. Evaluation of Performance of Bioreactors According to Number of Baffles and Presence or Absence of Channel Holes On the support of a tray, a photosynthetic bioreactor comprising five or six baffles/channel holes, or a photosynthetic bioreactor comprising only five or six baffles was hang. Then, a gas tube for injecting an air containing 3-5% carbon dioxide was connected to the gas inlet, after which water, culture medium and *Chlorella vulgaris* were sequentially injected into each of the reactors through the tube, followed by culture.

TAP-C (consisting of 0.5M TRIS base, nutrient stock, phosphate buffer, Kutner, and HCl) was used as the culture medium, the change in pH by injection of potassium hydroxide (KOH) and the spreading time of microalga after inoculation were measured during 18 days of culture.

As a result, it could be seen that the photosynthetic bioreactor having both the six channel holes and baffles showed the highest culture efficiency (FIGS. 13A and 13B).

In addition, the amount of biomass produced in each of the photosynthetic bioreactor was measured, and as a result, it could be seen that the photosynthetic bioreactor having the six baffles and channels holes produced the largest amount of biomass (FIG. 14). Furthermore, the degree of growth of cells per unit area was analyzed using the following equation 1, and as a result, it could be seen that the degree of growth of cells increased in proportion to the number of the channel holes and baffles (FIG. 15).

$$\text{Degree of growth of cells per unit area} = (\text{reactor volume}) \times (\text{number of reactors in tray})/(\text{tray area}) \times (\text{amount of cells grown}). \quad \text{Equation 1}$$

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:
1. A large-scale photosynthetic bioreactor comprising multiple photosynthetic bioreactor unit of which each is connected in series or in parallel by an adhesive, the photosynthetic bioreactor unit comprising:
   (a) a culture vessel in which the photosynthesis of photosynthetic organisms occurs;
   (b) a multi-purpose inlet/outlet unit formed at the outer lower end of the culture vessel;
   (c) an external tube disposed outside the culture vessel and connected to the multi-purpose inlet/outlet unit;
   (d) an internal tube disposed inside the culture vessel and connected to the multi-purpose inlet/outlet unit; and
   (e) one or more baffles disposed in the culture vessel,
   wherein the baffle has one to five channel holes formed on the surface thereof, and the culture vessel is made of a transparent film, and
   wherein the one or more baffles is a plate-shaped baffle comprising:
   a pair of first edges disposed in parallel with each other and attached to an internal surface of the culture vessel; and a pair of second edges disposed perpendicular to the pair of first edges, separated from the internal surface of the culture vessel, and exposed to an internal space of the culture vessel.

2. The photosynthetic bioreactor of claim 1, further comprising a support formed at an upper end of the culture vessel.

3. The photosynthetic bioreactor of claim 1, wherein the transparent film is selected from the group consisting of a low-density polyethylene (LDPE) film, a film formed from a mixture of polyethylene terephthalate (PET) and casting polypropylene (PET+CPP), a polyacetal (POM) film, a polycarbonate (PC) film, a polyester sulfon (PES) film, a polyethylene (PE) film, a polyvinyl chloride (PVC) film, a polyethylene terephthalate (PET) film, a polypropylene (PP) film, a polyphenylene oxide (PPO=PPE) film, and a film formed from a mixture of low-density polyethylene, polyethylene terephthalate and nylon 8.

4. The photosynthetic bioreactor of claim 1, wherein the multi-purpose inlet/outlet unit is connected with a tube for performing a function selected from the group consisting of (a) introducing photosynthetic organisms and culture medium, (b) introducing a carbon dioxide-containing gas, (c) extracting a sample, and (d) discharging gases.

5. The photosynthetic bioreactor of claim 1, wherein the internal tube is a four-way sparger for the introduction of a carbon dioxide-containing gas.

6. The photosynthetic bioreactor of claim 1, wherein both side ends of the baffle are made of a polyethylene material.

7. The photosynthetic bioreactor of claim 1, wherein both lower ends of the culture vessel are thermally bonded in an oblique direction.

8. The photosynthetic bioreactor of claim 1, wherein the large-scale photobioreactor is configured to culture photosynthetic microorganisms with 500 to 1000 L of culture medium.

9. The photosynthetic bioreactor of claim 1, wherein the adhesive is square shape, wherein length of the adhesive is twice of the photosynthetic bioreactor unit, and horizontal length of the adhesive is 10 to 20 cm, and wherein the adhesive is made of transparent film while both side ends of the adhesive are made of a polyethylene material.

10. The photosynthetic bioreactor of claim 1, further comprising an auxiliary support installed at the lower end of the photosynthetic bioreactor.

* * * * *